(12) United States Patent
Melkent et al.

(10) Patent No.: US 8,202,216 B2
(45) Date of Patent: Jun. 19, 2012

(54) TISSUE RETRACTOR

(75) Inventors: Anthony J. Melkent, Memphis, TN (US); Kidong Yu, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 867 days.

(21) Appl. No.: 11/683,897

(22) Filed: Mar. 8, 2007

(65) Prior Publication Data

US 2008/0221394 A1 Sep. 11, 2008

(51) Int. Cl.
*A61B 1/32* (2006.01)

(52) U.S. Cl. .................................................. 600/215

(58) Field of Classification Search .......... 600/184–235; 606/86 A
See application file for complete search history.

(56) References Cited

U.S. PATENT DOCUMENTS

| | | | |
|---|---|---|---|
| 3,875,595 A | 4/1975 | Froning | |
| 4,545,374 A * | 10/1985 | Jacobson | 600/210 |
| 5,902,231 A | 5/1999 | Foley et al. | |
| 5,928,139 A * | 7/1999 | Koros et al. | 600/205 |
| 5,993,384 A | 11/1999 | Lunsford et al. | |
| 6,152,871 A | 11/2000 | Foley et al. | |
| 6,206,822 B1 | 3/2001 | Foley et al. | |
| 6,206,826 B1 | 3/2001 | Mathews et al. | |
| 6,217,509 B1 * | 4/2001 | Foley et al. | 600/114 |
| 6,425,859 B1 | 7/2002 | Foley et al. | |
| 6,520,907 B1 | 2/2003 | Foley et al. | |
| 6,679,833 B2 | 1/2004 | Smith et al. | |
| 6,945,933 B2 | 9/2005 | Branch et al. | |
| 7,001,333 B2 | 2/2006 | Hamel et al. | |
| 7,074,226 B2 | 7/2006 | Roehm, III et al. | |
| 2004/0143169 A1 * | 7/2004 | Branch et al. | 600/245 |
| 2005/0277812 A1 * | 12/2005 | Myles | 600/231 |
| 2006/0155170 A1 * | 7/2006 | Hanson et al. | 600/201 |

* cited by examiner

*Primary Examiner* — Eduardo C Robert
*Assistant Examiner* — Steven Cotroneo (57) ABSTRACT

Methods and devices for minimally invasive surgery in a patient. A tubular body is disclosed which includes in its side wall a plurality of longitudinal passages. Elongated blocking members are also disclosed which are inserted into the passages. The elongated blocking members block deflected interfering tissue during the surgery.

36 Claims, 8 Drawing Sheets

TISSUE RETRACTOR

FIELD OF THE INVENTION

This invention relates to devices, instruments and methods for performing percutaneous surgeries. More specifically, this invention is an improvement in the field of minimally invasive surgery.

BACKGROUND

Severe back pain, limited motion, and nerve damage may be caused by injured, degraded, or diseased spinal anatomy. Affected spinal joints, and particularly discs and ligaments, can be difficult to treat externally and may necessitate surgery. Traditional surgical procedures for pathologies located deep within the body can cause significant trauma to the intervening tissues. These open procedures often require a long incision, extensive muscle stripping, prolonged retraction of tissues, denervation and devascularization of tissue.

Some minimally invasive alternatives, such as arthroscopic, endoscopic and micro-surgical techniques, can reduce the destruction of healthy tissue. The site of a pathology is accessed through portals rather than through a significant incision, thus preserving the integrity of the intervening tissues. These minimally invasive techniques often require only local anesthesia, thus avoiding general anesthesia with its increased expense, post-operative recovery time and risk. Minimally invasive surgical techniques are particularly desirable for spinal and neurosurgical applications because of the need for access to locations deep within the body and the potential range of damage to vital intervening tissues.

Various configurations of tissue retractors have been used to reposition and protect non-targeted soft tissue, muscle and neural elements. Improvements to the devices and methods of tissue retraction are still needed.

SUMMARY

This invention offers an improved system, apparatus and method for performing tissue retraction during a percutaneous surgery. In one exemplary aspect, this disclosure is directed to a retractor body having a side wall longitudinally extending between proximal and distal ends of the retractor body, the side wall having formed therein one or more passages extending between the proximal and distal ends of the retractor body, the distal end of the retractor body being insertable into a patient to a surgical site.

In another aspect, an elongated blocking member is disclosed which is distally insertable through one of the passages in a manner causing a distal end portion of the elongated blocking member to project outwardly through the distal end of the retractor body and block the return of the deflected tissue to its original position relative to the inserted distal end of the retractor body.

In some embodiments, location, quantity and cross-section of the passages are varied. Other embodiments vary the properties of the body such as wall thickness, distal-end tapering and overall cross-section.

A method is disclosed to teach the steps of accessing a surgical site in a patient by first forming an opening through the patient's skin. A tubular body with a central working channel and distal end is inserted into the opening. An interfering tissue underlying the working channel at the distal end of the tubular body is displaced laterally and outwardly away from the center of the distal end. An elongated blocking member is then passed through a passage in the tubular body. The elongated blocking member is extended beyond the distal end of the tubular body to block laterally inward movement of the displaced tissue.

These and other features will become apparent from the following description.

BRIEF DESCRIPTION OF THE DRAWINGS

FIGS. 9-12*a*, 13 and 14 are proximal end views of tubular bodies according to various exemplary embodiments.

DETAILED DESCRIPTION

The present disclosure relates to devices, instruments and methods for performing percutaneous surgery. More particularly, the present disclosure describes an improvement in the field of minimally invasive surgery.

For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Figure 1:
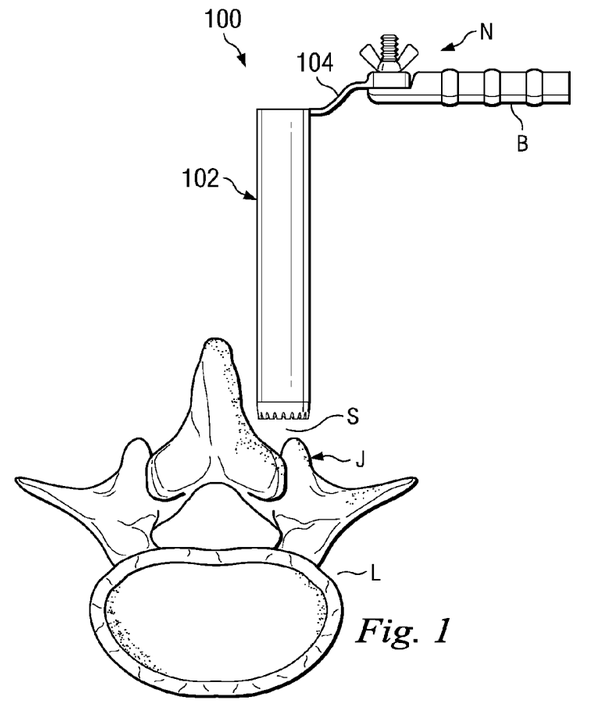
FIG. 1 is an axial view of the tissue retraction system inserted via a posterior approach to access a spinal joint according to one exemplary embodiment.

Referring first to FIG. 1, an axial view of a spinal cross-section L and a tissue retraction system 102 inserted via a posterior approach are shown generally. Surgical site S refers to a general area adjacent to a spinal joint J. The tissue retractor system 102 is shown in one exemplary configuration 100. In this configuration 100, the tissue retractor system 102 has a mounting bracket 104 which is fixedly attached to a flexible support arm B via a bolt and wing nut N. Flexible support arm B is mounted to a surgical table.

Figure 2:
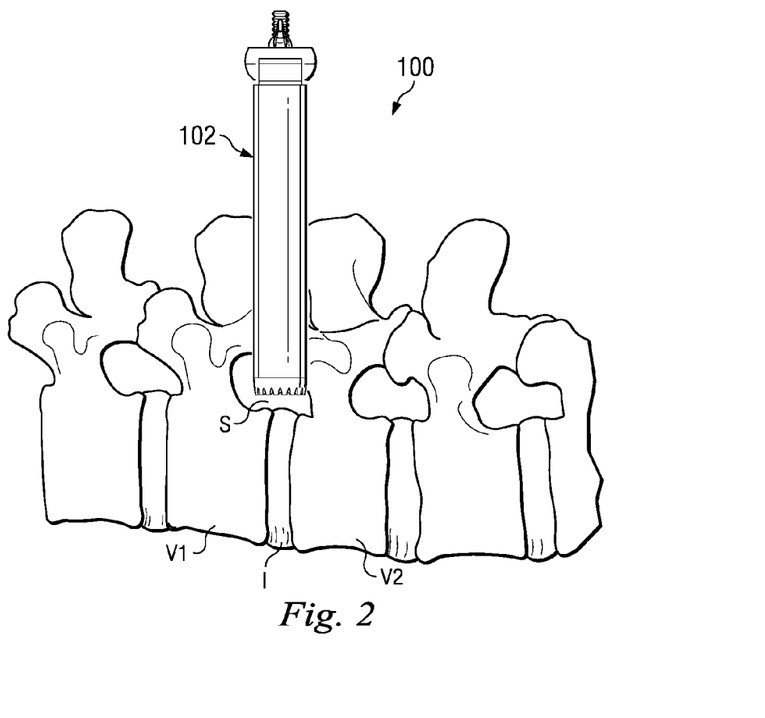
FIG. 2 is a side view of the tissue retraction system inserted via a posterior approach to access a spinal joint according to one exemplary embodiment.

A further aspect of this configuration 100 is shown in FIG. 2, where surgical site S is positioned above spinal disc I. Spinal disc I is shown bounded by vertebral bodies V1 and V2. This configuration contemplates a surgical treatment of, or near spinal disc I. In the illustrated exemplary embodiment, the position of the tissue retractor system 102 is generally vertical and oriented to provide protected access to surgical site S. It will be appreciated by one skilled in the art that a portion of system 102 will be visible outside of the body of the patient when the tissue retractor system 102 is fully positioned for a surgical procedure.

Figures 3, 4, 5, 6:
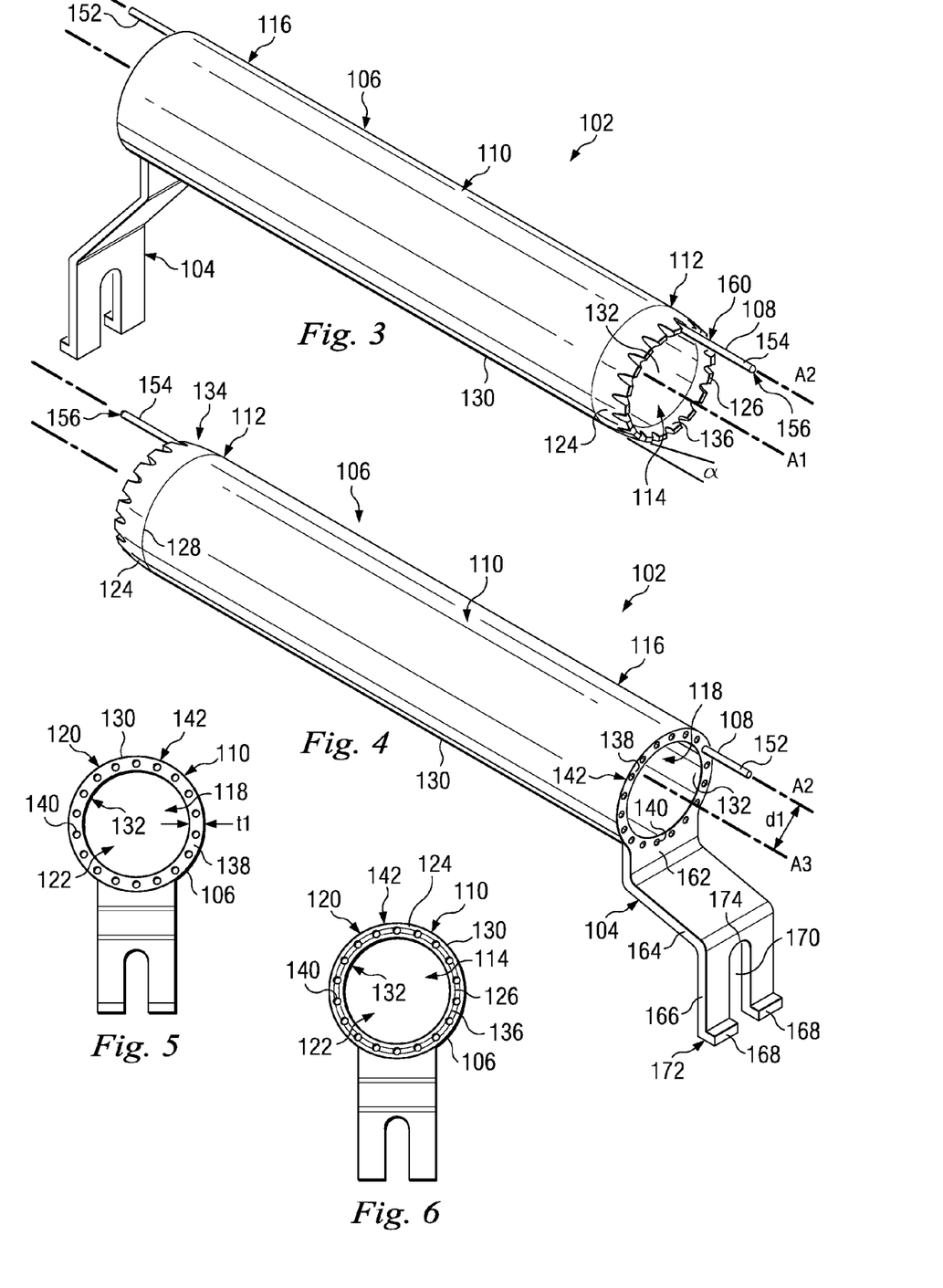
FIG. 3 is a perspective view showing the distal end of a tubular body according to one exemplary embodiment.
FIG. 4 is a perspective view showing the proximal end of the tubular body shown in FIG. 3.
FIG. 5 is a proximal end view of the tubular body shown in FIG. 4.
FIG. 6 is a distal end view of the tubular body shown in FIG. 4.

Now referring to FIGS. 3-6, the tissue retractor system 102 is shown. The tissue retractor system 102 according to this exemplary embodiment comprises a tubular body 106, mounting bracket 104 and elongated blocking member 108. As shown in FIG. 3, the tubular body 106 has a side wall 110 which circumscribes a longitudinal axis A1. Tubular body 106 extends longitudinally along axis A1 from distal end 112 with distal end opening 114 to proximal end 116 with proximal end opening 118. FIGS. 5 and 6 show that this embodiment has a tubular body 106 with a circular cross-section 120. A working channel 122 extending between distal end opening 114 and proximal end opening 118 is laterally bounded by side wall 110, thus providing a protected space through which to access a percutaneous surgical site. As shown in FIG. 5, the side wall 110 has a thickness t1.

A further aspect of this embodiment is shown in FIG. 3. The distal end 112 has an external taper 124. The external taper 124 terminates in the distal face 126 of the tubular body 106 and effectively reduces the surface area of the distal face 126 and the diameter of the tubular body 106. The reduced surface area of the distal face 126 and wedge-shape of the distal end 112 enable the tubular body 106 to be introduced to the surgical site S with greater facility and with less trauma to interfering, or non-target tissues. FIG. 6 shows the distal end view of the tubular body 106. In this embodiment 100, the external taper 124 begins at a location 128 on the outer surface 130 of the side wall 110 and travels inwardly at an angle α thereby preventing the external taper 124 from intersecting with an inner surface 132 of the side wall 110 before terminating in the distal end 112. An additional feature of the external taper 124, as best seen in FIG. 4, is that the outer surface of the external taper 124 includes as arcuate portion in addition to the tapering outer surface. The arcuate portion 134 of the external taper 124 can also be seen in FIG. 7. In yet another embodiment, the external taper intersects an inner surface of a side wall at a distal end of a tubular body, thereby establishing only a nominal surface area on the distal face. It is further contemplated that the external taper 124, or the distal end 112 may include longitudinal flutes, radii or other design features to enhance the functionality of the tissue retractor system 102.

An additional aspect of this embodiment is shown in FIG. 3, where in addition to external taper 124, the distal end 112 has an internal taper 136. The internal taper 136 begins at the inner surface 132 of the side wall 110 and travels distally toward the outer surface 130 of the side wall 110 before it terminates in the distal face 126 of the tubular body 106, thereby further reducing the surface area of distal face 126. FIG. 6 shows the distal face 126 with a reduced surface area. A proximal face 138 shown in FIG. 5, is comparable in surface area to a distal face which is unreduced by internal and external tapers. Internal taper 136 can work independently of, or in conjunction with, the external taper 124. The internal taper 136 shown is linear but it can be arcuate. In yet another embodiment, internal and external tapers intersect, thereby establishing only a nominal surface area on a distal face. The internal taper 136 or distal end 112 may include longitudinal flutes, radii or other design features to enhance the functionality of the tissue retractor system 102. Additionally, the inner surface 132 or the outer surface 130 of the side wall 110 at the distal end 112 may include longitudinal flutes, radii or other design features. The remaining surface of the distal face 126, accounting for the presence or absence of any tapers, can be blunt, sharp or curved as required.

A further aspect of this embodiment is the inclusion of a circumferentially spaced plurality of passages 140 formed in the side wall 110. The circumferential spacing places the passages 140 around the periphery 142 of the tubular body 106. The passages 140 extend longitudinally between the proximal and distal ends 116, 112 of the tubular body 106, generally parallel to the longitudinal axis A1. In this embodiment, the central axis A2 of each passage 140 is located a fixed distance d1 from the longitudinal axis A1. Each passage 140 is circular in cross-section and sized to provide a clearance fit for an elongated blocking member 108. The elongated blocking member 108 is introduced into a passage 140 at the proximal end 116 of the tubular body 106 and advanced distally beyond the distal end 112 of the tubular body 106. The proximal face 138 is shown as generally planar. The passage 140 may also have a varying cross-section, or a non-circular, square, rectangular, triangular or other cross-sectional shape. In one embodiment, a passage has a substantially dove-tail shaped cross-section (see FIG. 12a, 254). In a further embodiment, a passage has a cam-shaped, or eccentric, cross-section designed to cooperate with a similarly enabled elongated blocking member. In the illustrated embodiments, there are one or more passages. In another embodiment the plurality of passages is replaced by a single passage.

Figure 7:
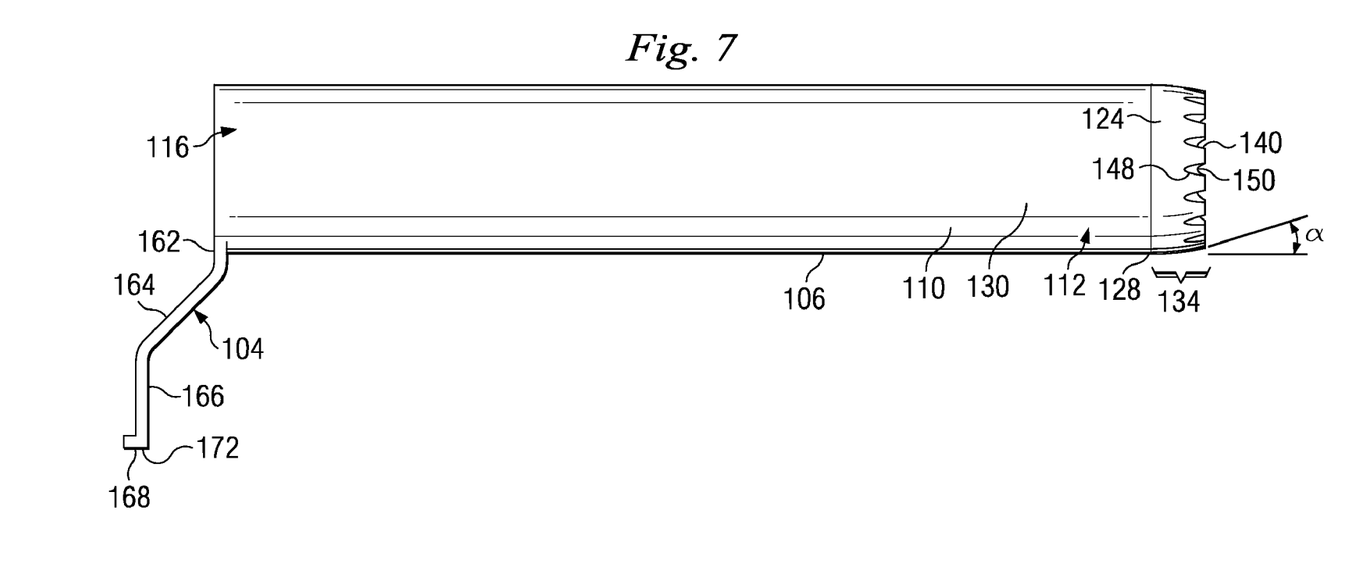
FIG. 7 is a side view of the tubular body shown in FIG. 4.
Figure 8:
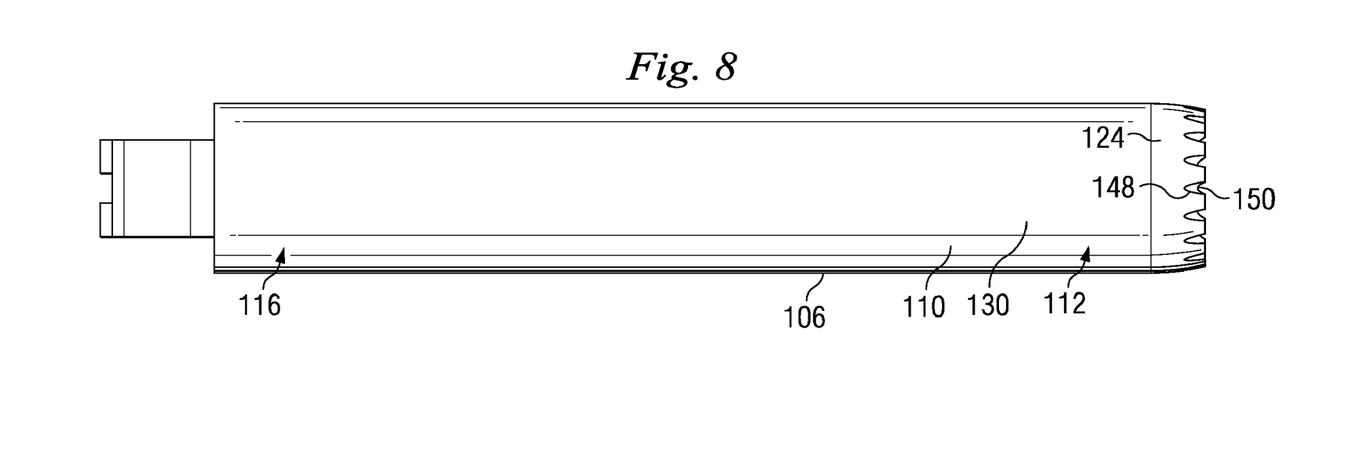
FIG. 8 is a top view of the tubular body shown in FIG. 7.

FIGS. 7 and 8 show a side and top view, respectively, of the tubular body 106 and mounting bracket 104. The external taper 124 is visible in both side and top views, however, the internal taper is not directly visible in either view. The distal end of the passages 140 is shaped by the external taper 124 and internal taper of this embodiment. Angle α of the external taper 124 creates an external scallop 148 at the intersection of a surface of the external taper 124 with the distal end of the passage 140. The angle of the internal taper surface causes an internal scallop 150 at intersection with the distal end of the passage 140. The scallops 148, 150 of the distal face 126 further reduce the surface area presented by the distal face 126 during insertion into a patient. It will be appreciated by one skilled in the art that the external and internal scallops 148, 150 shown in FIGS. 7 and 8 may be increased or decreased by, among other variations, altering the angle of the tapers or by varying the wall thickness t1 of the side wall 110.

Alternative arrangements of the passages 140 include variations in number of passages 140, variations in spacing between passages 140 and variations in cross-sections. FIG. 5, for example, shows the proximal end 116 of tubular body 106 having eighteen evenly spaced passages 140 of equal and consistent cross-section. It is contemplated that a particular configuration of passages 140 consists of a plurality of two or more passages. Another configuration consists of a plurality of more than eighteen passages. The spacing between passages may be even or irregular. The passages may be grouped in a certain section, such as in a particular quadrant, or in multiple sections of the side wall. The cross-section of a single passage may also vary over its length. The cross-section of a plurality of passages may be variable or equal.

Each passage 140 is substantially configured to cooperate with an elongated blocking member 108, as shown in FIG. 3. The passage 140 provides a clearance fit for the intended elongated blocking member 108 of substantially matching cross-section. Each elongated blocking member 108 extends longitudinally between a proximal end 152 and a distal end 154. An atrautmatic tip 156 at the distal end 154 may contact certain tissues, and as such, may be designed to be atraumatic to prevent tissue injury. The atraumatic tip 156 further prevents the tip from penetrating into bone while also inhibiting damages to soft tissues. Other tip configurations are contemplated, such as, for example, blunt, rounded, or tapered. A further variation provides a distal end 154 with a penetrating tip, whereby the distal end 154 is pointed, allowing the elongated blocking member to penetrate certain types of durable body tissues such as cartilage or bone for securing the tubular body. The atraumatic tip 156 can be further prepared with knurling, threads, or lateral grooves. A rod-shaped elongated member may also be a K-wire, a guide wire or an anchor wire. An elongated blocking member 108 may also have a varying cross-section or a non-circular cross-section, or as needed to match the cross-section of a passage. In one embodiment, an elongated blocking member has a substantially dove-tail shaped cross-section (see FIG. 12b). In a further embodiment, an elongated blocking member has a cam-shaped, or eccentric, cross-section. In a further variation, the tubular body comes pre-assembled with elongated blocking members fixed in a first state, wherein their distal tips are substantially disposed within a side wall. The elongated blocking members are selectively released from the first state, and then extended distally through passages in the side wall. The elongated blocking members are then fixed in a second state to block interfering tissue. In one embodiment, the elongated blocking members are fixed by rotation inside an eccentric passage. Rotation in an opposite direction loosens the friction fit and permits longitudinal movement of the elongated blocking members. Other fixing and releasing means are also contemplated.

Figures 21, 22:
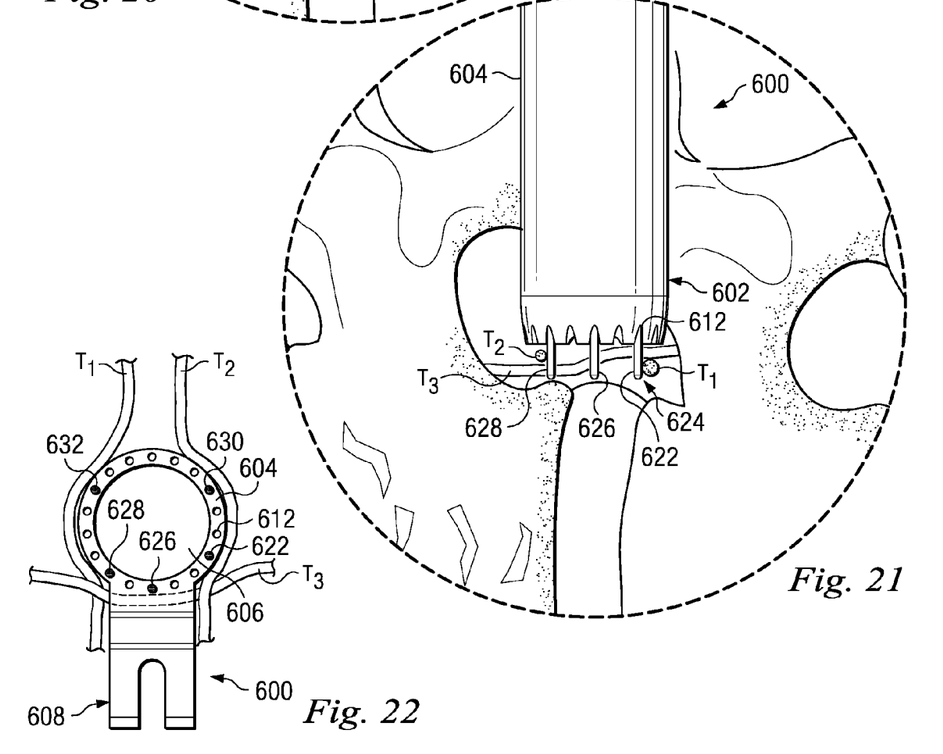
FIG. 21 is a side view showing the completed displacement and retention of the interfering tissue being maintained by elongated blocking members.
FIG. 22 is a proximal end view representing the improved operating field after retraction of all interfering tissues.
Figure 23:
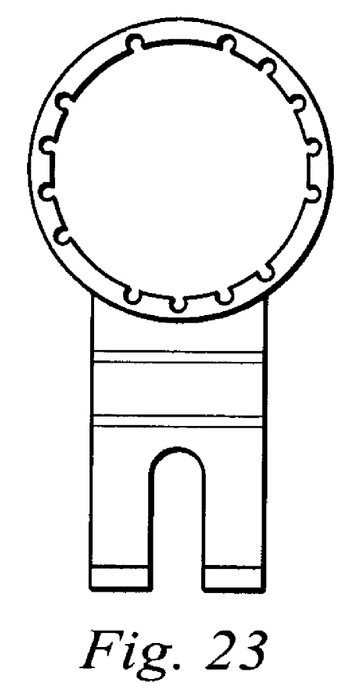
FIG. 23 is a proximal end view of a tubular body with passages arranged in an unequal spaced pattern.
Figure 24:
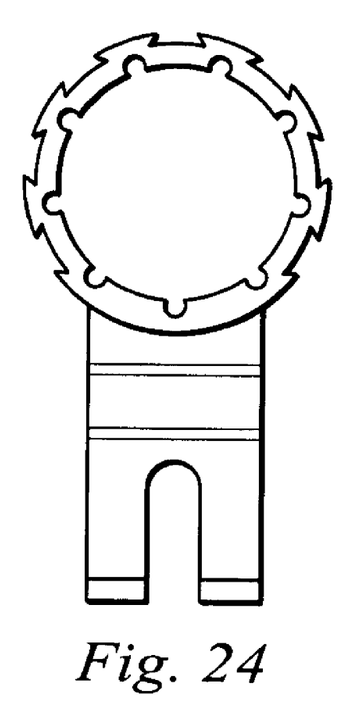
FIG. 24 is a proximal end view of a tubular body with at least two passages varying in cross-sectional shape.

Once beyond the distal end 112 of the tubular body 106, the elongated blocking member 108 is used to maintain the displacement of, or the blocking of, the return of deflected, non-target, or interfering tissue (see FIG. 22 and related description below). After obtaining a blocking position 160 as shown in FIG. 3, the proximal end 152 of the elongated blocking member 108 may be bent around the proximal end 116 of the tubular body 106 to secure the elongated blocking member 108. Alternatively, the elongated blocking member 108 may be secured by other fastening means, such as with a collar and set screw. A further fastening means is accomplished by the rotation of an elongated blocking member 108 having a cam-shaped, or eccentric, cross-section. The rotation of a cam-shaped elongated blocking member changes the clearance fit between the passage 140 and the elongated blocking member 108 to create a friction fit there between.

A mounting bracket 104 is shown in FIGS. 3-5 and 7, integrally attached to the proximal end 116 of the tubular body 106. This mounting bracket 104 is fastened to a flexible support arm B, which can be of known design. Preferably, the flexible support arm B is engaged to the mounting bracket 104 by way of a bolt and wing nut N, as shown in FIG. 1; although, other engaging means are contemplated. The flexible support arm B is mounted to the surgical table and is readily adjusted into a fixed position to provide firm support for the tissue retractor system 102. The flexible support arm B can be contoured as required to stay clear of the surgical area, thereby allowing surgeons adequate room to manipulate the variety of tools that are used throughout the procedure.

The mounting bracket 104 has lateral portion 162, riser portion 164, mounting portion 166, and locking tabs 168. The lateral portion 162 is adjacently positioned near the proximal end 116, and is integral with, the tubular body 106 in this embodiment. The lateral portion 162 is generally co-planar with the proximal face 138, allowing the surgeon more operating space around the proximal end 116. In other embodiments a lateral portion is fixedly attached to, but is not integral with, a tubular body. In a further variation not illustrated, a lateral portion is attached to a location distal from the proximal end of a tubular body. The riser portion 164 attaches to the lateral portion 162 and extends proximally away from the tubular body 106, further clearing the surgical working area. In one embodiment, a riser portion extends away from a lateral portion in a proximal and lateral direction. A mounting portion 166 attaches to the riser portion 164 and extends in a generally perpendicular direction away from the tubular body 106 with respect to the longitudinal axis A1. The mounting portion 166 is generally planar with a slot 170 extending from an edge 172 of the mounting portion 166 opposite of the riser portion to a slot length 174. At the edge 172 of the mounting portion 166, locking tabs 168 attach and extend in a generally perpendicular direction relative to the mounting portion 166.

Figure 9:
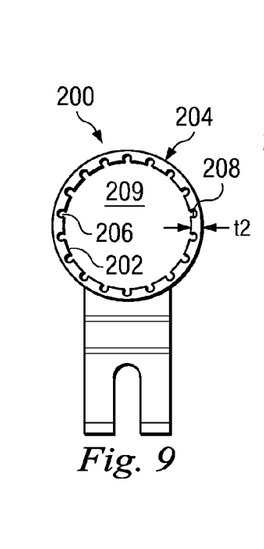
Figures 10, 11:
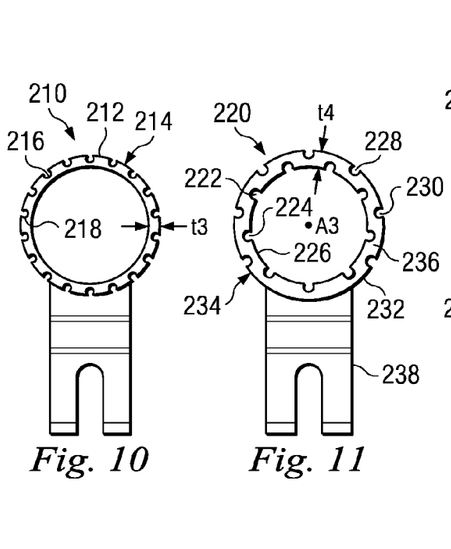

Now referring to FIGS. 9 and 10, the proximal end views of various exemplary embodiments are shown. FIG. 9 shows an assembly 200 having longitudinally extending passages 206 similar to passages 140 previously described above. In the illustrated embodiment, the passages have a diameter, and wall thickness t2 that is less than the diameter of the passages 206. The centers of the passages 206 are closer to the inner surface 202 of the tubular body 204. The resulting passages 206 have lateral openings 208 through the inner surface 202 in communication with internal working channel 209. Alternatively, the wall thickness t2 may be less than the thickness of an elongated blocking member.

FIG. 10 shows an additional assembly 210, wherein a tubular body 214 has passages 216, which passages have a diameter. The wall thickness t3 is less than the diameter of the passages 216. The center of the passages 216 is closer to the outer surface 212, resulting in passages 216 having lateral openings 218 extending through the outer surface 212. Alternatively, the thickness t3 may be less than the thickness of an elongated blocking member.

Now referring to FIG. 11, a proximal end view of an assembly 220 according to one exemplary embodiment is shown. In this embodiment, a tubular body 234 has inner passages 222, wherein the inner passages 222 have lateral openings 224 through the inner surface 226. The tubular body 234 also has outer passages 228, wherein the outer passages 228 have lateral openings 230 through the outer surface 232. The centers of the passages 222, 228 are at varying distances from the central longitudinal axis A3 of the tubular body 234. In the illustrated embodiment, the internal passages 222 are uniformly spaced around the interior. The outer passages 228 are radially spaced between the inner passages 222, except where mounting bracket 238 joins the tubular body 234. In other configurations, the thickness t4 of side wall 236 may be varied to expose more or less of the inner passages 222 or more or less of the outer passages 228. In other embodiments, the spacing between passages may vary.

Figure 12A:
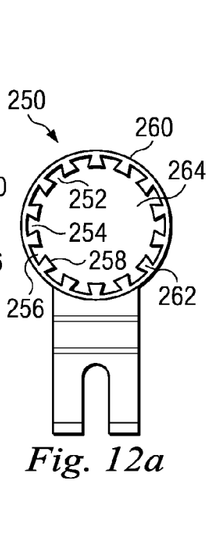
Figure 12B:
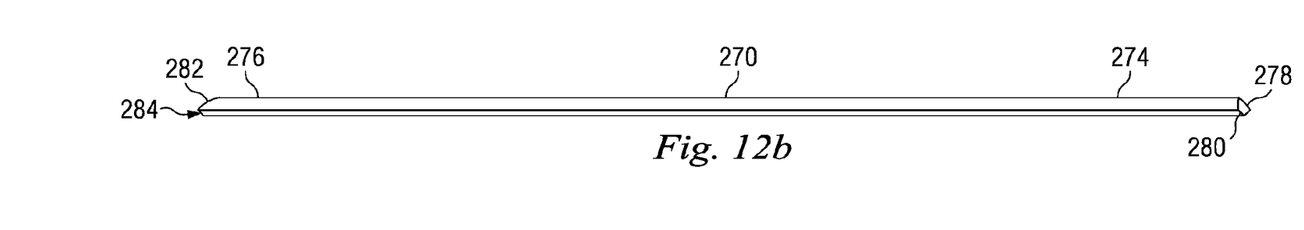
FIG. 12*b* is a side view of an elongated blocking member for use in conjunction with the embodiment shown in FIG. 12*a*.

Now referring to FIGS. 12a and 12b, a further embodiment is shown. FIG. 12a shows the proximal end view of an assembly 250, wherein passages 252 have a generally dove-tailed cross-section 254. The passages 252 have lateral openings 256 through inner surface 258 and communicate with the working channel 264. Alternatively, the passages may be oriented to an outer surface 260, thereby exposing a lateral opening in the outer surface 260. In a further embodiment, dove-tailed passages are completely disposed within the thickness of a side wall, resulting in a completely enclosed passage and in no lateral opening through inner or outer surfaces.

FIG. 12b is a side view of an elongated blocking member for use in conjunction with the assembly shown in FIG. 12a. Elongated blocking member 270 has a generally dove-tailed cross-section shaped and sized for being received within and for cooperation with passages 252. The elongated blocking member 270 has proximal end 274 and distal end 276. Elongated blocking member 270 is further defined by broad edge 278 and narrow edge 280. When elongated blocking member 270 is installed in passage 252, the narrow edge 280 faces the working channel 264 of the tubular body 234. The broad edge 278 is laterally constrained in the side wall 262, thus allowing longitudinal movement only. Distal end 276 is further enhanced with a radius 282 which travels proximally starting from the distal end 276 at the narrow edge 280 and feathering into the broad edge 278. Radius 282 forms an atraumatic tip 284 for blocking member 270. Other embodiments include an elongated blocking member with a blunt or ball-shaped distal end.

Figure 13:
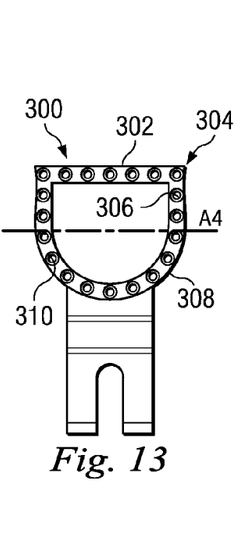
Figure 14:
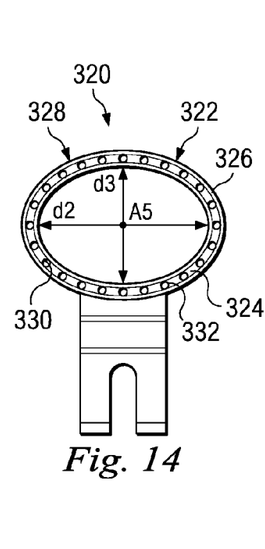

Now referring to FIGS. 13 and 14, proximal end views according to two exemplary embodiments with varied cross-sections are shown. FIG. 13 shows an assembly 300 with one flat side wall 302 forming a d-shaped cross-section 304. Included passages 306 are asymmetrical about axis A4, and disposed circumferentially about the periphery 308 as shown. A further aspect shown in this proximal end view is that the passages 306 have tapered openings 310, such as, for example, counter-sinks to facilitate the engagement of an elongated blocking member. Further embodiments include side walls with more than one flat side, and passages which are asymmetrical about more than one axis.

FIG. 14 shows an assembly 320. An oval-shaped cross-section 322 is defined by a circular shape with diameter d2 perpendicular to diameter d3, both crossing through axis A5. Diameter d2 is greater than diameter d3 in this embodiment. A further aspect shown in this proximal end view is a continuous, annular groove 324 which is formed in an entire proximal face 326 of the tubular body 328 with its maximum root depth aligned through the center 330 of a plurality of passage openings 332. The groove 324 facilitates the engagement of an elongated blocking member. Other shapes and cross-sections are also contemplated.

Figures 15, 16:
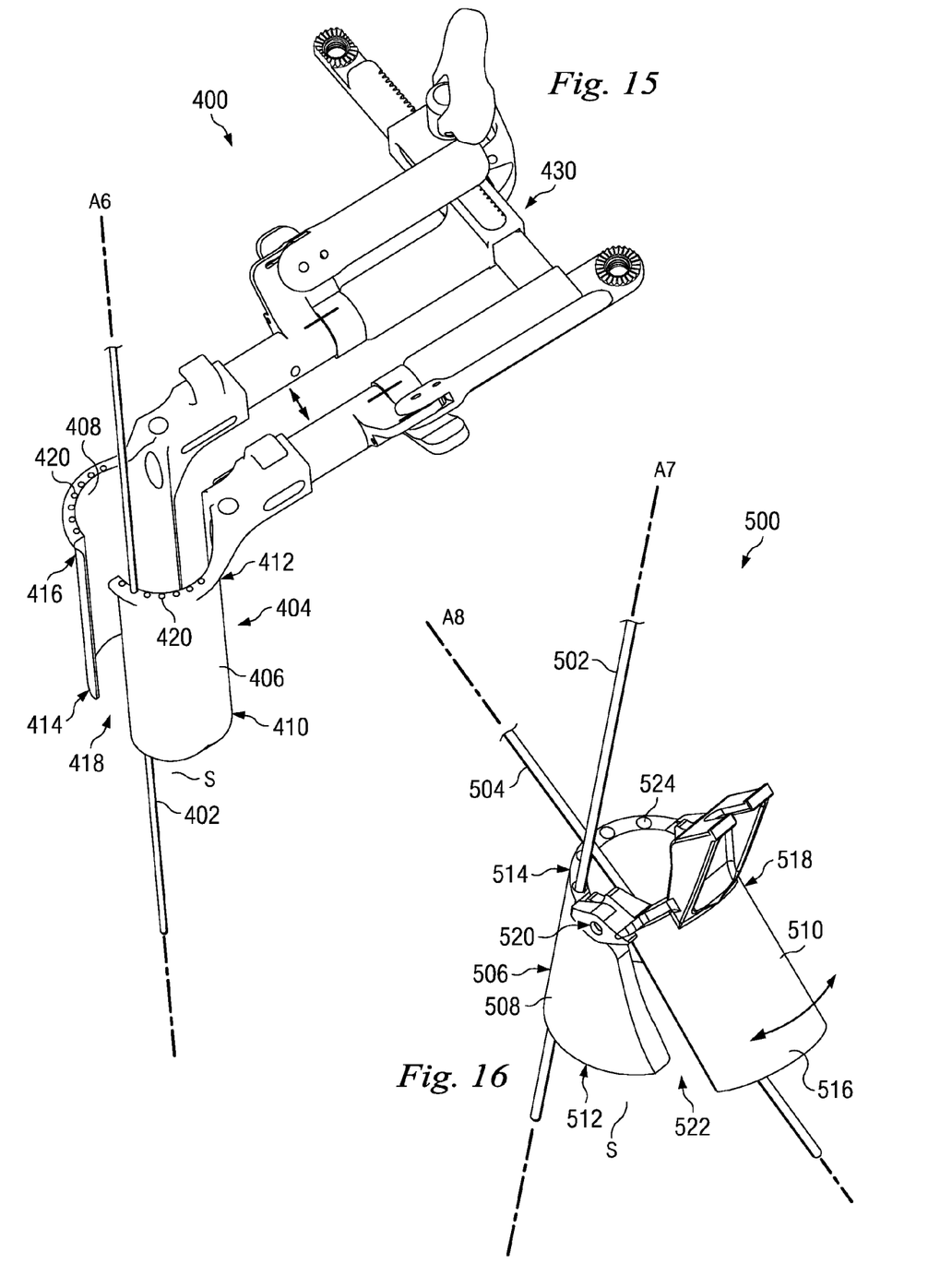
FIG. 15 is a perspective view of an elongated blocking member being used in conjunction with a variable width main body tube, according to one exemplary embodiment.
FIG. 16 is a perspective view of an elongated blocking member being used in conjunction with a main body tube, according to one exemplary embodiment.

FIG. 15 shows a perspective view of an elongated blocking member 402 designed for use in conjunction with a variable width main body tube 404, according to one exemplary assembly 400. In this embodiment, the main body tube 404 has a first blade 406 and a second blade 408. Body blades 406, 408 have an arcuate cross section with a concave inner surface and a convex outer surface. In other embodiments, the blades have other configurations such as flat, curved or other geometries. First blade 406 has a distal end 410 and an opposite proximal end 412. Second blade 408 has a distal end 414 and an opposite proximal end 416. A working channel 418 is formed between first blade 406 and second blade 408. After insertion into a patient, the working channel 418 is enlarged by spreading first blade 406 and second blade 408 apart by operation of the rack and pinion assembly 430. In other embodiments, a single blade is used. In yet a further embodiment, more than two blades are used.

Separation of first and second blades 406, 408 increases the size of working channel 418, thereby providing greater access to a surgical site S. A plurality of passages 420 extend longitudinally between the proximal ends 412, 416 and the distal ends 410, 414 respectively. In this embodiment, each passage 420 is circular in cross-section and sized to provide a clearance fit for elongated blocking member 402. The elongated blocking member 402 shown is positioned in passage 420 of the first blade 406. Elongated blocking member 402 is used to maintain the displacement of, or to block the return of, deflected, non-target, interfering tissue (see FIG. 22, and description below). Elongated member 402 is substantially aligned with axis A6, as are passages 420. As installed, multiple elongation members 402 will be generally parallel to each other. As described previously, elongated blocking member 402 is secured in position by one or more of various fastening means.

FIG. 16 shows a perspective view of elongated blocking members 502, 504 designed for use in conjunction with a laterally expandable main body tube 506, according to one exemplary assembly 500. In this embodiment, a main body tube 506 has a first portion 508 and a second hinged portion 510. First portion 508 has a distal end 512 and an opposite proximal end 514. Second hinged portion 510 has a distal end 516 and an opposite proximal end 518. Second hinged portion 510 is rotatably attached at the proximal end 518 via a hinge 520 to the proximal end 514 of the first portion 508. A working channel 522 is formed between first portion 508 and second hinged portion 510. After insertion into a patient, the distal end portion of working channel 522 is enlarged by rotating second hinged portion 510 away from first portion 508.

Rotation of second hinged portion 510 increases the size of the distal end portion of working channel 522, thereby providing greater access to a surgical site S. A plurality of passages 524 extend longitudinally between the proximal ends 514, 518 and the distal ends 512, 516 of the first and second portions 508, 510. In this embodiment, each passage 524 is circular in cross-section and sized to provide a clearance fit for elongated blocking members 502, 504. The elongated blocking member 502 is shown positioned in a passage 524. As positioned, the elongated blocking member 502 of the first portion 508 is generally aligned with axis A7. Additionally, as positioned, the elongated blocking member 504 is generally aligned with axis A8. Axis A8 aligns generally longitudinally with second hinged portion 510. Thus, in this embodiment the correlative orientation of the elongated blocking members 502, 504 may range from substantially parallel to substantially perpendicular.

Once positioned, the elongated blocking member 502 is used to maintain the displacement of, or to block the return of deflected, non-target, interfering tissue (see FIG. 22, and description below). As described previously, the elongated blocking members 502, 504 is secured in position by one or more of various fastening means.

Figure 20:
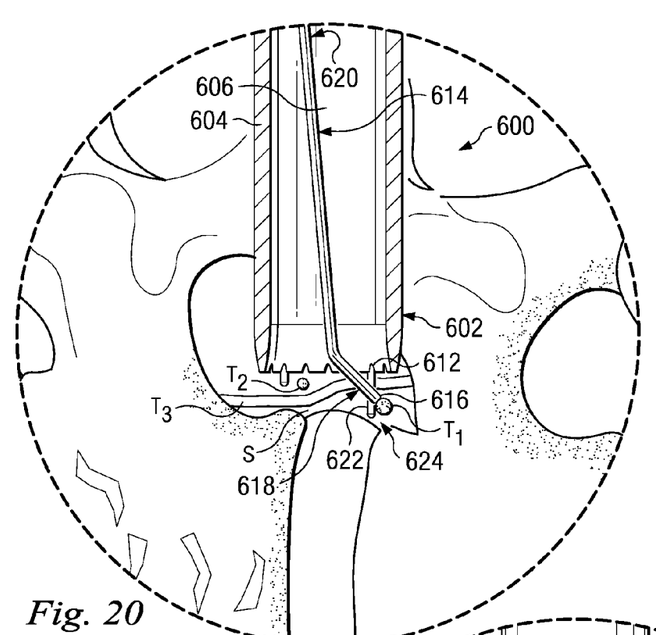
FIG. 20 is a side view showing a retractor tool displacing an interfering tissue while an elongated blocking member is installed.

Referring briefly to FIG. 20, a further included component of tissue retractor system 600 is a retractor tool 614. The retractor tool 614 includes a working tip 616 configured to atraumatically displace tissue as the retractor tool 614 is manipulated. The retractor tool 614 further has a distal first end 618 and a proximal second end 620, wherein the distal first end 618 has an integral working tip 616. The working tip 616 is preferably blunt, and bent or curved away from the distal first end 618. The retractor tool 614 is removably and rotatably insertable through a working channel 606. As shown in FIG. 20, the retractor tool 614 is positioned with a portion distally extendable through a tubular body 604 and being operative to engage and selectively deflect interfering tissue at a surgical site laterally outwardly from an inserted distal end 602 of the tubular body 604.

Additional means for laterally deflecting the interfering tissue include various surgical tools such as, for example, a nerve root retractor tool, a nerve hook tool, a surgical probe tool, a curette tool, or a push-and-pull tool. The retractor tool 614 may also be designed to minimize obstruction of the surgeon's visualization of and access to the working space at the distal end 602 of the tubular body 604. Further description of the retractor tool 614 is found in the description of the method below.

In order to describe the specific operation of this embodiment, the method of establishing this system in a ready position will now be described. As seen in FIGS. 1 and 2, embodiments of the invention are utilized from a substantially midline or medial posterior approach to the spine. Of course, it is understood that many of the following surgical steps can be performed from other approaches to the spine, such as posterolateral, lateral, anterior and anterolateral.

In a first step of the technique, an opening is made through a patient's skin. Referring generally to FIGS. 17-21, a tissue retractor system 600 is shown. The distal end 602 is inserted into the opening in the patient's skin. The tubular body 604 of the tissue retractor system 600 is carefully advanced through the opening until the distal end 602 of the tubular body 604 is adjacent a surgical site S.

Alternatively, a sequential dilation method is used to position the tissue retractor system 600. A method such as that described by U.S. Pat. No. 6,520,907 (incorporated herein by reference) is instructive of this method. As a first step, a guidewire is advanced through the skin and tissue adjacent the laminae of a vertebral body. A series of concentric tissue dilators are then advanced over the guidewire to enlarge the opening. Alternatively, the dilators are advanced through a small opening without the aid of a guidewire. The advancing of successively larger dilators concentrically disposed over each other serves to sequentially dilate the perispinous soft tissues. Ultimately, a tubular body, or cannula is advanced over the largest dilator, followed by removal of the dilators and guidewire.

With the tubular body 604 in position, a generally unobstructed working channel 606 is formed. Alternatively, the method of inserting a tubular body 604 is accomplished by using a tubular body with an oval-shaped or d-shaped cross-section, among other cross-sections. It is understood that the longitudinal length of the tubular body 604 is determined by the particular surgical operation being performed, and by the anatomy surrounding the working space.

In one embodiment, the tissue retractor system 600 is comprised of a mounting bracket 608 affixed to the outer surface 610 of the tubular body 604. The mounting bracket 608 is fastened to a flexible support arm B (see FIG. 1), which can be of known design. The flexible support arm B is secured to the mounting bracket 608 by way of a bolt and wing nut N, as shown in FIG. 1, although other securing means are contemplated. The flexible support arm B is mounted to a rigid support on the surgical table and is readily adjusted into a fixed position to provide firm support for the tubular body 604. The flexible support arm B is contoured as required to stay clear of the surgical area, thus providing adequate room to manipulate the variety of tools that are used throughout the procedure. Additionally, the tubular body 604 is readily positioned and centered over an appropriate target tissue or bone. In another embodiment, one or more passages is used to contain anchor wires, which anchor wires can penetrate the patient's bone to fix the position of a tubular body directly to the body of a patient, thereby making the use of a mounting bracket and support arm optional.

Figure 17:
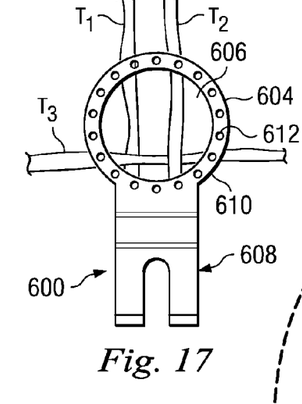
FIG. 17 is a proximal end view of a tubular body according to another aspect showing exemplary, non-target spinal tissue.
Figure 18:
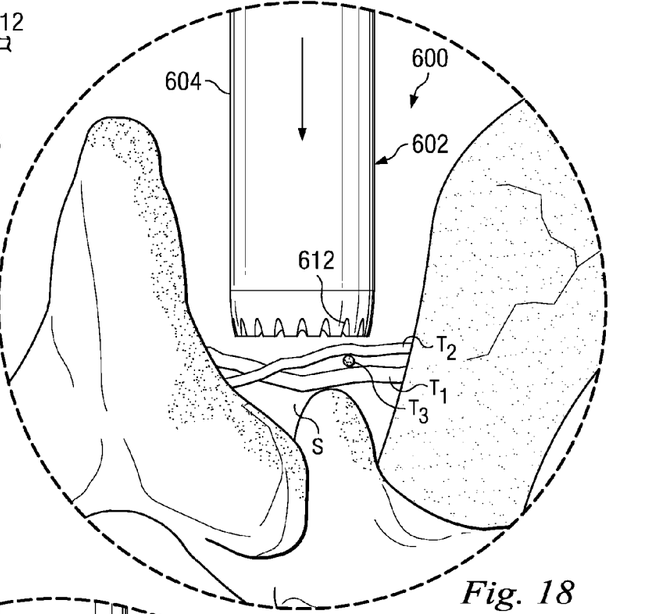
FIG. 18 is an axial view of the embodiment shown in FIG. 17, illustrating use adjacent to the spine.
Figure 19:
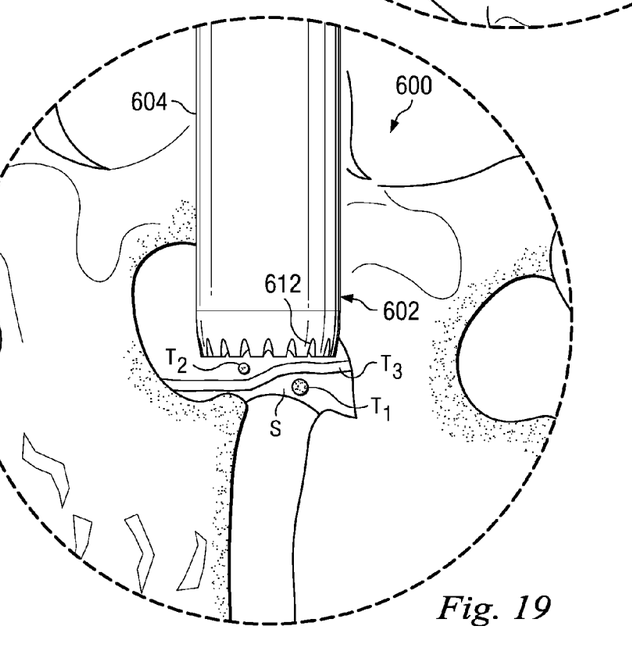
FIG. 19 is a transverse side view of the embodiment shown in FIG. 18 rotated 90 degrees.

Once the position of the tubular body 604 is established and the working channel 606 is oriented over the proper target tissue, a variety of tools and instruments are extended through the working channel, thereby re-positioning of important tissues. FIG. 17 shows an end view looking distally towards the surgical site S through the working channel 606 of tubular body 604. In this simplified representation, several tissues T1, T2 and T3 are encumbering the surgeon's view and access to the surgical site S. FIG. 18 shows a side view of the scenario depicted in FIG. 17. FIG. 18 shows a rotated side view of the non-target, or interfering tissues T1, T2, T3 encumbering the surgical site S. Tissues T1, T2 and T3 may represent any type or combination of structure including, but not limited to, nerves, blood vessels, ligaments or muscles.

As shown in FIG. 20, a retractor tool 614, as described previously, is inserted from the proximal end of tubular body 604 toward the distal end of the tubular body 604. The retractor tool 614 is used to engage and selectively deflect a first interfering tissue T1 laterally outwardly from the inserted distal end 602 of the tubular body 604. The retractor tool 614 is removably and rotatably insertable through the working channel 606. The retractor tool 614 includes a working tip 616 configured to atraumatically displace tissue as the retractor tool 614 is manipulated. The retractor tool 614 further has a distal first end 618 and a proximal second end 620 which is integral with the working tip 616. The working tip 616 preferably has a blunt end which is bent or curved away from the distal first end 618. In some embodiments the step of manipulating a retractor tool 614, is performed with a known surgical tool such as, for example, a nerve root retractor tool, a nerve hook tool, a surgical probe tool, a curette tool, or a push-and-pull tool.

While the first interfering tissue T1 is held in a deflected position laterally outward from the distal end 602, an elongated blocking member 622 is introduced distally into a passage 612. The blocking member is advanced from the proximal end of passage 612 through the tubular body 604 and beyond the distal end 602. The step of introducing an elongated blocking member may be performed using an elongated blocking member with an atraumatic tip.

Elongated blocking member 622 is positioned at a sufficient distal depth beyond the distal end 602 of tubular body 604 to prevent the return of tissue T1. After obtaining a blocking position 624 as shown in FIG. 20, the proximal end of the elongated blocking member 622 may be bent around the proximal end of the tubular body 604 to secure the elongated blocking member 622. Alternatively, the elongated blocking member 622 may be secured longitudinally by other fastening means, such as with a collar and set screw. A further fastening means is accomplished by the rotation of an elongated blocking member having a cam-shaped, or eccentric, cross-section. The rotation of a cam-shaped elongated blocking member changes the clearance fit between a passage and an elongated blocking member into a friction fit.

After securing the elongated blocking member 622 in blocking position 624, the retractor tool 614 may be released from contact with tissue T1. A second tissue T2 is next deflected by the retractor tool 614 and subsequently blocked by addition of elongated blocking member 626, as shown in FIG. 21. A third exemplary tissue T3 is next deflected by the retractor tool 614 and subsequently blocked by addition of an elongated blocking member 628.

The steps of deflecting interfering tissues with a tool and blocking tissue return with an elongated blocking member are repeated until the surgical site S is unobstructed by interfering tissues, at which time the retractor tool 614 may be removed. FIG. 22 shows the unobstructed surgical site S, accomplished by blocking exemplary interfering tissues T1, T2, T3 with elongated blocking members 622, 626, 628, 630 and 632.

The cleared surgical site S facilitates the pending surgical procedure which may be, for example, a laminotomy, laminectomy, foramenotomy, facetectomy, or discectomy, among other procedures. In some instances, graft material is passed through the working channel of a tubular body into the disc space. In other procedures, graft material or bone chips are positioned across posterior aspects of the spine using a movement of a tubular body to different angles from a single opening in the skin. In one alternative, the step of performing a surgical procedure comprises inserting an implant through the working channel of a tubular body, the implant being one of a spinal spacer, a spinal fixation device, a motion preservation device, or a therapeutic agent. The therapeutic agent may be a biologic agent to enhance bone growth or a pharmaceutical agent.

In one alternative method, the entire tissue retractor system or a component thereof may be disposed of after a single surgical procedure, the material of the components being degradable upon sterilization or made brittle upon exposure to sterilizing radiation. In another embodiment, the tubular body and at least one passage are formed by extrusion.

One method of manufacturing the tubular body is by extruding it from a biocompatible material. The tubular body, bracket, retractor tool, and elongated blocking member may be formed of any suitable biocompatible material including, for example, metals such as cobalt-chromium alloys, titanium alloys, nickel titanium alloys, aluminum, and/or stainless steel alloys. In one embodiment, the tissue retractor system 102 is formed of a cobalt-chrome-molybdenum metallic alloy (ASTM F-799 or F-75). Ceramic materials such as aluminum oxide or alumina, zirconium oxide or zirconium, compact of particulate diamond, and/or pyrolytic carbon may also be suitable. Polymer materials may also be used alone or in combination with reinforcing elements, including any member of the polyaryletherketone (PAEK) family such as polyetheretherketone (PEEK), carbonreinforced PEEK, or polyetherketoneketone (PEKK); polysulfone; polyetherimide; polyimide; ultra-high molecular weight polyethylene (UHMWPE); cross-linked UHMWPE; and/or polycarbonate, among others. In some embodiments, different features, such as the elongated blocking members and tubular body, are formed of dissimilar materials. In other embodiments, the entire tissue retractor system is formed of a single material.

According to one embodiment, instruments and techniques for conducting a variety of surgical procedures are provided. In the illustrated embodiments, these procedures are conducted on the spine. However, the same devices and techniques can be used at other places in the body, such as the brain. The present embodiments have particular value for percutaneous procedures where minimal invasion into the patient is desirable, and where clear surgical site is required or desired. Other potential areas of application are the pituitary regions, the gastro-intestinal tract, etc.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. In the claims, means-plus-function clauses are intended to cover the elements described herein as performing the recited function and not only structural equivalents, but also equivalent elements.

We claim:

1. A tissue retractor system comprising:
 a tubular body having a side wall circumscribing a longitudinal axis and longitudinally extending between open proximal and distal ends of the tubular body, the side wall having formed therein a circumferentially spaced plurality of passages extending between the proximal and distal ends of the tubular body, the distal end of the tubular body being insertable into a patient to a surgical site;
 a retractor tool having a portion distally extendable through the tubular body and being operative to engage and selectively deflect tissue at the surgical site laterally outwardly beyond the inserted distal end of the tubular body;
 an elongated blocking member distally insertable through one of the passages in a manner causing a distal end portion of the blocking member to project outwardly beyond the distal end of the tubular body and to block return of the retractor-tool-deflected tissue to its original position relative to the inserted distal end of the tubular body,
 the distally extendable portion of the retractor tool being configured to permit operative insertion of the elongated blocking member during tissue-deflection use of the retractor tool; and
 passages with counter-sunk openings at the proximal end.

2. The tissue retractor system according to claim 1, wherein the tubular body has a wall thickness greater than a thickness of the elongated blocking member.

3. The tissue retractor system according to claim 1, wherein the tubular body has inside and outside surfaces extending between the proximal and distal ends, and where at least one passage is completely disposed between the inside and outside surfaces.

4. The tissue retractor system according to claim 1, wherein the tubular body has a wall thickness less than a thickness of the elongated blocking member.

5. The tissue retractor system according to claim 1, wherein the tubular body has one or more planar wall portions.

6. The tissue retractor system according to claim 1, wherein the spacing pattern of the passages is asymmetrical.

7. The tissue retractor system according to claim 1, wherein the tubular body is substantially oval shaped.

8. The tissue retractor system according to claim 1, wherein the tubular body is constructed substantially of biocompatible material.

9. The tissue retractor system according to claim 1, wherein the tubular body is an extrusion.

10. The tissue retractor system according to claim 1, wherein the tubular body is separable into two substantially equal blades.

11. The tissue retractor system according to claim 1, wherein the tubular body has a laterally separable portion hinged at the proximal end, and wherein the tubular body is expandable by rotating the distal end of the hinged portion away from the longitudinal axis of the tubular body.

12. The tissue retractor system according to claim 1, wherein the elongated blocking member includes an atraumatic distal tip.

13. The tissue retractor system according to claim 1, wherein the tubular body has inside and outside surfaces extending between the proximal and distal ends, and where at least one passage laterally opens along a substantial portion of the length of the at least one passage through the inside surface.

14. The tissue retractor system according to claim 1, wherein the tubular body has inside and outside surfaces extending between the proximal and distal ends, and where at least one passage laterally opens along a substantial portion of the length of the at least one passage through the outside surface.

15. The tissue retractor system according to claim 1, wherein the tubular body has inside and outside surfaces extending between the proximal and distal ends, and where at least one passage opens laterally along a substantial portion of the length of the at least one passage through the inside surface, and at least another one of the passages opens laterally along a substantial portion of the length of the at least one passage through the outside surface.

16. The tissue retractor system according to claim 1, wherein at least one of the passages has a generally dovetail-shaped cross-section.

17. The tissue retractor system according to claim 1, further comprising an integral mounting bracket.

18. The tissue retractor system according to claim 1, further comprising a means for limiting longitudinal movement of at least one elongated blocking member relative to the tubular body.

19. A tissue retractor system comprising:
a tubular body having a side wall circumscribing a longitudinal axis and longitudinally extending between open proximal and distal ends of the tubular body, the side wall having formed therein a circumferentially spaced plurality of passages extending between the proximal and distal ends of the tubular body, the distal end of the tubular body being insertable into a patient to a surgical site;
a retractor tool having a portion distally extendable through the tubular body and being operative to engage and selectively deflect tissue at the surgical site laterally outwardly from the inserted distal end of the tubular body; and
an elongated blocking member distally insertable through one of the passages in a manner causing a distal end portion of the blocking member to project outwardly beyond the distal end of the tubular body and to block return of the retractor-tool-deflected tissue to its original position relative to the inserted distal end of the tubular body,
the distally extendable portion of the retractor tool being configured to permit operative insertion of the elongated blocking member during tissue-deflection use of the retractor tool, and further comprising a continuous, circumferential groove formed in the entire proximal face of the tubular body with its maximum root depth aligned through the center of the passage openings.

20. The tissue retractor system according to claim 19, wherein the tubular body has a wall thickness greater than a thickness of the elongated blocking member.

21. The tissue retractor system according to claim 19, wherein the tubular body has inside and outside surfaces extending between the proximal and distal ends, and where at least one passage is completely disposed between the inside and outside surfaces.

22. The tissue retractor system according to claim 19, wherein the tubular body has a wall thickness less than a thickness of the elongated blocking member.

23. The tissue retractor system according to claim 19, wherein the tubular body has one or more planar wall portions.

24. The tissue retractor system according to claim 19, wherein the spacing pattern of the passages is asymmetrical.

25. The tissue retractor system according to claim 19, wherein the tubular body is substantially oval shaped.

26. The tissue retractor system according to claim 19, wherein the tubular body is constructed substantially of biocompatible material.

27. The tissue retractor system according to claim 19, wherein the tubular body is an extrusion.

28. The tissue retractor system according to claim 19, wherein the tubular body is separable into two substantially equal blades.

29. The tissue retractor system according to claim 19, wherein the tubular body has a laterally separable portion hinged at the proximal end, and wherein the tubular body is expandable by rotating the distal end of the hinged portion away from the longitudinal axis of the tubular body.

30. The tissue retractor system according to claim 19, wherein the elongated blocking member includes an atraumatic distal tip.

31. The tissue retractor system according to claim 19, wherein the tubular body has inside and outside surfaces extending between the proximal and distal ends, and where at least one passage laterally opens along a substantial portion of the length of the at least one passage through the inside surface.

32. The tissue retractor system according to claim 19, wherein the tubular body has inside and outside surfaces extending between the proximal and distal ends, and where at least one passage laterally opens along a substantial portion of the length of the at least one passage through the outside surface.

33. The tissue retractor system according to claim 19, wherein the tubular body has inside and outside surfaces extending between the proximal and distal ends, and where at least one passage opens laterally along a substantial portion of the length of the at least one passage through the inside surface, and at least another one of the passages opens laterally along a substantial portion of the length of the at least one passage through the outside surface.

34. The tissue retractor system according to claim 19, wherein at least one of the passages has a generally dovetail-shaped cross-section.

35. The tissue retractor system according to claim 19, further comprising an integral mounting bracket.

36. The tissue retractor system according to claim 19, further comprising a means for limiting longitudinal movement of at least one elongated blocking member relative to the tubular body.

* * * * *